United States Patent [19]
Laube et al.

[11] Patent Number: 5,320,094
[45] Date of Patent: Jun. 14, 1994

[54] METHOD OF ADMINISTERING INSULIN

[75] Inventors: Beth L. Laube, Baltimore, Md.; G. Kenneth Adams, III, Bloomfield, N.J.; Angeliki Georgopoulos, Minneapolis, Minn.

[73] Assignee: The Johns Hopkins University, Baltimore, Md.

[21] Appl. No.: 819,234

[22] Filed: Jan. 10, 1992

[51] Int. Cl.$^5$ .................. A61M 15/00; A61M 16/10; A61M 11/00; A62B 7/00
[52] U.S. Cl. .......................... 128/203.12; 128/200.24; 128/200.14; 128/200.21; 128/200.23
[58] Field of Search .................... 128/200.14, 200.24, 128/203.12, 200.23, 200.21

[56] References Cited

U.S. PATENT DOCUMENTS

| | | |
|---|---|---|
| 2,788,784 | 4/1967 | Birch et al. |
| 2,944,546 | 7/1960 | Ziherl et al. ............ 128/205.17 |
| 4,119,097 | 10/1978 | Spector. |
| 4,484,577 | 11/1984 | Sackner et al. ........... 128/203.28 |
| 4,534,343 | 8/1985 | Nowacki et al. .......... 128/200.23 |
| 4,612,929 | 9/1986 | Boiarski et al. .......... 128/200.21 |
| 4,624,251 | 11/1986 | Miller ..................... 128/200.14 |
| 4,635,627 | 1/1987 | Gam ....................... 128/200.14 |
| 4,677,975 | 7/1987 | Edgar et al. ............. 128/203.12 |
| 4,790,305 | 12/1988 | Zoltan .................... 128/200.23 |
| 4,796,614 | 1/1989 | Nowacki et al. .......... 128/200.14 |
| 4,829,996 | 5/1989 | Noakes et al. ........... 128/200.14 |
| 4,929,852 | 5/1990 | Zoltan et al. ............ 128/200.23 |
| 5,027,806 | 7/1991 | Zoltan et al. ............ 128/200.23 |

FOREIGN PATENT DOCUMENTS

| | | |
|---|---|---|
| 0933216 | 12/1947 | France. |
| 1524904 | 11/1989 | U.S.S.R. ................. 128/200.24 |
| 2110543 | 6/1983 | United Kingdom ........ 128/200.23 |

OTHER PUBLICATIONS

Harrison & Cantab; Insulin in Alcoholic Solution by the Mouth; The British Medical Journal; Dec. 22, 1923 pp. 1204–1205.

Shichiri et al; Increased Intestinal Absorbtion of Insulin in a Micellar Solution; Water-in-Oil-in-Water Insulin Micelles; First Department of Medicine; Oct. 20, 1977; pp. 175–183.

Newman et al; Deposition of Pressurised Aerosols in the Human Respiratory Tract; Department of Medical Physics; 1981; pp. 52–55.

Wigley, et al–Insulin Across Respiratory Mucosae by Aerosol Delivery–Diabetes, vol. 20, No. 8, Aug., 1971, pp. 552–556.

Elliott et al–Parental Absorption of Insulin from the Lung in Diabetic Children–Aust. Paediatr. J. (1987), pp. 293–297.

Primary Examiner—Edgar S. Burr
Assistant Examiner—Kimberly L. Asher
Attorney, Agent, or Firm—Cushman, Darby & Cushman

[57] ABSTRACT

A method of delivering a protein, in particular insulin, to the lungs. The method is characterized in that an aerosolized mist of small particles is produced in an associated medicament delivery chamber, the distance from the chamber to the patient's mouth is set to slow the speed of aerosol particles entering the mouth and the flow rate through the chamber is regulated to a low rate of less than about 30 liters per minute. It has been found that administering insulin in accordance with the invention may advantageously produce a penetration of medication into the lungs of about 90%.

3 Claims, 3 Drawing Sheets

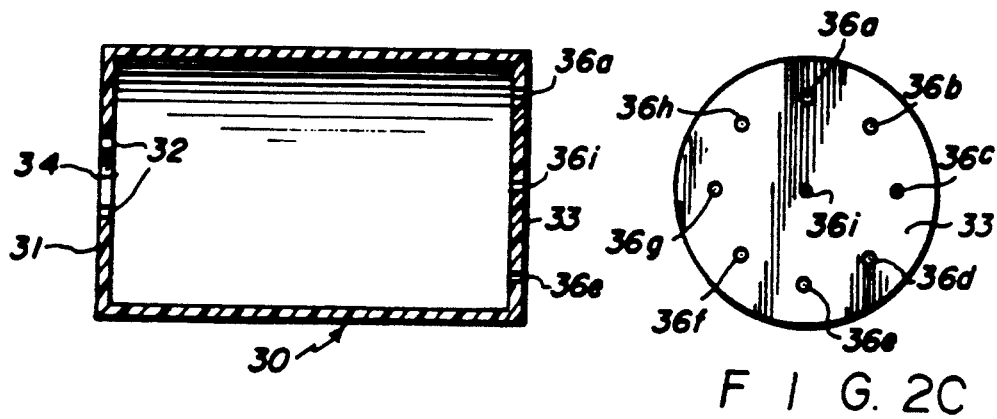
FIG. 2B (PRIOR ART)
FIG. 2C (PRIOR ART)
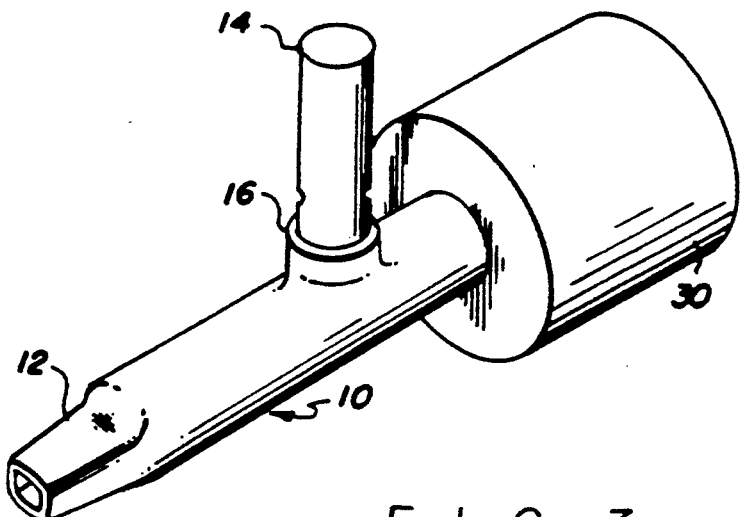
FIG. 3 (PRIOR ART)

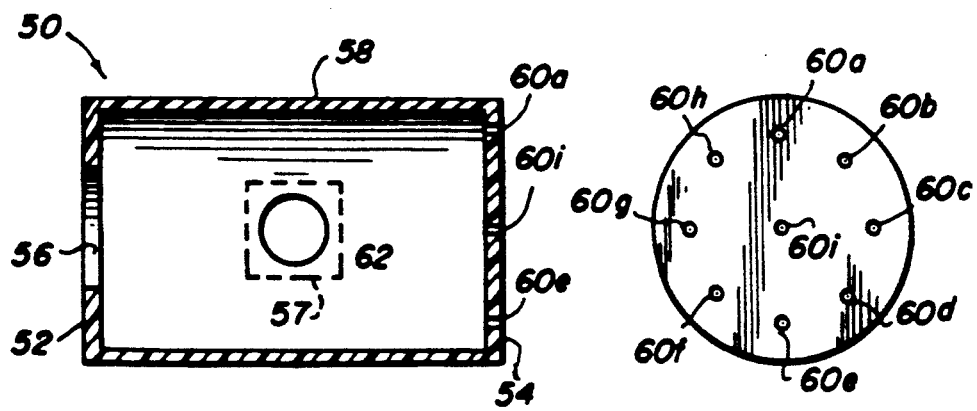
FIG. 4A (PRIOR ART)
FIG. 4B (PRIOR ART)
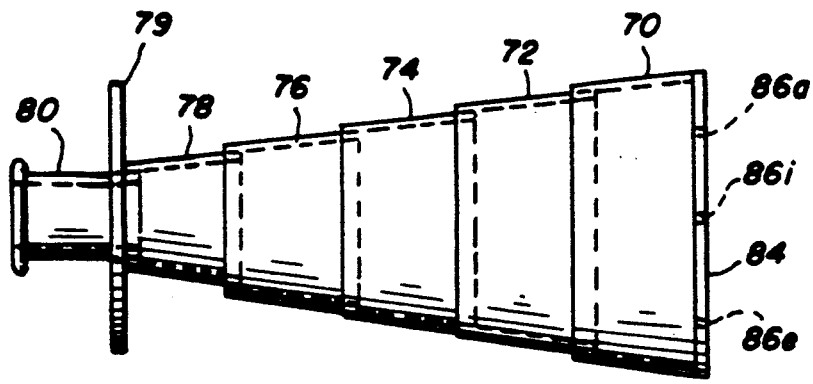
FIG. 5A (PRIOR ART)
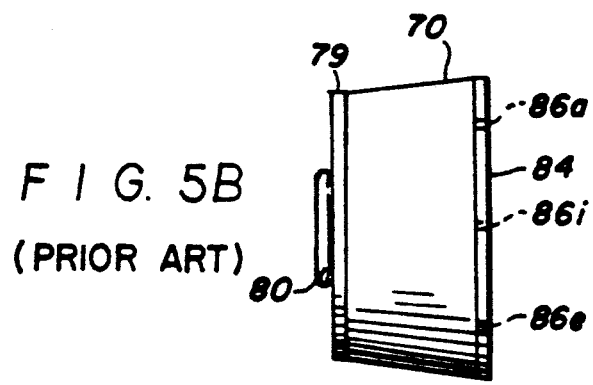
FIG. 5B (PRIOR ART)

METHOD OF ADMINISTERING INSULIN

BACKGROUND OF THE INVENTION

The physical discomfort associated with subcutaneous injection of insulin causes many type II diabetic patients to refuse insulin therapy entirely, while type I patients may refuse intensive treatment. A number of investigators have explored various alternative routes of administration of insulin in the hope of developing a substitute for injection.

Harrison and Cantab, "Insulin in Alcoholic Solution by Mouth", *Br Med J*, pp. 1204-1205 (1923), and Shichiri et al, "Increased Intestinal Absorption of Insulin in a Micellar Solution: water-in-oil-in-water insulin micelles", *Acta Diabetol Lat*, 15:175-183 (1978), examined the effect of delivering insulin enterically on blood glucose levels in humans and rabbits, respectively. Harrison et al. found that oral administration in alcohol would be too uncertain and too expensive to be of little therapeutic value in treating diabetics. Similarly, Shichiri et al. showed that the possibility of insulin absorption in a micellar form was impractical, since a reduction in blood glucose was only accomplished through intrajejunal administration and the required dose was 25-50 times that of an intramuscular dose.

Yamasaki et al, "The Effectiveness of Rectal Administration of Insulin Suppository in Normal and Diabetic Subjects", *Diabetes Care*. 4:454-458 (1981), tested the effectiveness of insulin administration by rectal suppository in normal and non-insulin-dependent non-obese diabetic subjects. They found that a dose 10 times the subcutaneous dose was necessary to lower blood glucose levels significantly, and some subjects complained of abdominal discomfort or a feeling of rectal urgency.

N. F. Fisher, "The Absorption of Insulin from the Intestine, Vagina, and Scrotal sac", *Am J Physiol*, 67:65-71 (1923), found that blood glucose levels in dogs were only temporarily reduced when insulin was administered through fistulae into the intestine or through vaginal administration. He found that scrotal administration of insulin resulted in a more sustained lowering of blood glucose in rabbits than with the other two routes of administration. However, this method of insulin delivery required injection into the scrotal sac and was not recommended for treatment of human diabetic patients.

Moses et al., "Insulin Administered Intranasally as an Insulin-bile salt Aerosol. Effectiveness and Reproducibility in Normal and Diabetic Subjects", *Diabetes* 32:1040-1047 (1983) reported that insulin administered intranasally as a bile-salt aerosol was effective in lowering blood glucose levels in diabetic subjects. Nevertheless, the amount of insulin absorbed through the nasal mucosa was approximately 10% of the dose delivered by intravenous injection and 2.5 times the subcutaneous dose was required to lower blood glucose. In addition, subjects reported nasal irritation and nasal congestion following administration, probably due to the presence of the bile acid.

Because of lower serum absorption and/or local irritation, none of these alternative routes of administration have been developed to replace insulin injection in the treatment of diabetes.

Creasia et al., "Efficacy of Inhaled Insulin: Effect of Adjuvant",*FASEB J*. 2: A537 (1988), and Almer et al. "Insulin Inhalation—at last a break-through", Diabetes Research and Clinical Practice, XIII Congress of the International Diabetes Federation: Sydney, Australia, S163 (1988), demonstrated that insulin aerosol delivered through the rat lung was effective in lowering serum glucose. Wigley et al., "Insulin Across Respiratory Mucosae by Aerosol Delivery", *Diabetes*, 20:552-556 (1971), and Elliott et al., "Parenteral Absorption of Insulin from the lung in Diabetic Children", *Aust Paediatr J*. 23:293-297 (1987), showed that insulin delivered to the human lung as an aerosol crosses the respiratory mucosa and retains biologic activity, since plasma insulin levels increased after insulin inhalation and blood glucose levels were lowered. Nevertheless, only one patient in the Wigley study achieved a normal blood glucose level following insulin inhalation, and none of the patients in the Elliott study responded with lowering of the blood glucose to within the normal range. The authors concluded that variable and inefficient absorption of insulin across the lung mucosa could account for their results. The dose of insulin available for inhalation at the mouth and the distribution of the available dose within the respiratory tract were not quantified in either study.

All U.S. patents and publications referred to herein are hereby incorporated by reference.

SUMMARY OF THE INVENTION

The inventors have discovered that it is possible to administer insulin as an orally inhaled aerosolized medication. An aerosol mist of small particles is produced in a medication delivery chamber. The distance from the chamber to the inhalation mouthpiece is set to slow the speed of aerosol particles entering the mouth and the respiratory flow rate is regulated at low rates. This combination of features are produced by providing an inhalation spacer and means for regulating the flow rate into the patient's mouth to a rate of below about 30 liters per minute. It has been found that administering insulin in accordance with the invention may advantageously produce a penetration of medication into the lungs of about 90%.

BRIEF DESCRIPTION OF THE DRAWINGS

FIG. 1A is a perspective view of the mouthpiece which may be advantageously used in accordance with the method of the invention;

FIG. 1B is a cross-sectional view of the mouthpiece of FIG. 1A;

FIG. 2A is a view of the rigid chamber which may be advantageously used in accordance with the method of the invention;

FIG. 2B is a cross-sectional view of the chamber of FIG. 2A;

FIG. 2C is a detailed elevational view of the apertures in the end of the rigid chamber;

FIG. 3 is a perspective view of the assembled device;

FIG. 4A is a cross-sectional view of an alternate device which may be advantageously used in accordance with the method of the invention;

FIG. 4B is an elevational view of the end of the chamber of FIG. 4A;

FIG. 5A is an elevational view of another alternate device which may be advantageously used in accordance with the method of the invention; and FIG. 5B shows the device of FIG. 5A in its collapsed configuration.

DETAILED DESCRIPTION OF THE PRESENTLY PREFERRED EXEMPLARY EMBODIMENTS

The present inventors hypothesized that another explanation for the poor response to insulin delivered to the lungs as an aerosol in the above-noted previous studies by Wigley et al and Elliott et al was an inadequate dose of insulin, as the result of loss of drug in the delivery system and/or in the oropharynx. In experiments described below, the inventors used an aerosol delivery system that maximized deposition within the lungs. The inventors then determined the number of actuations and inhalations necessary to administer a mean dose of approximately 0.2 U/kg body weight (BW) of aerosolized insulin to the mouth using this delivery system, and monitored the plasma glucose response in normal subjects and non-insulin dependent diabetic (NIDDM) subjects. They chose to deliver 0.2 U/kg body weight (BW) because this is the dose given by subcutaneous administration.

In accordance with the currently preferred method, a particular medication delivery system, described in U.S. Pat. No. 4,926,852, is used to achieve the low flow rate which the inventors have discovered is critical to the effective delivery of insulin, in particular, to the lungs. The preferred device is illustrated in FIGS. 1-5. The device includes a medication chamber for receiving a protein, or the like, an outlet aperture through which the material is withdrawn and flow rate limiting orifices.

Figure 1A:
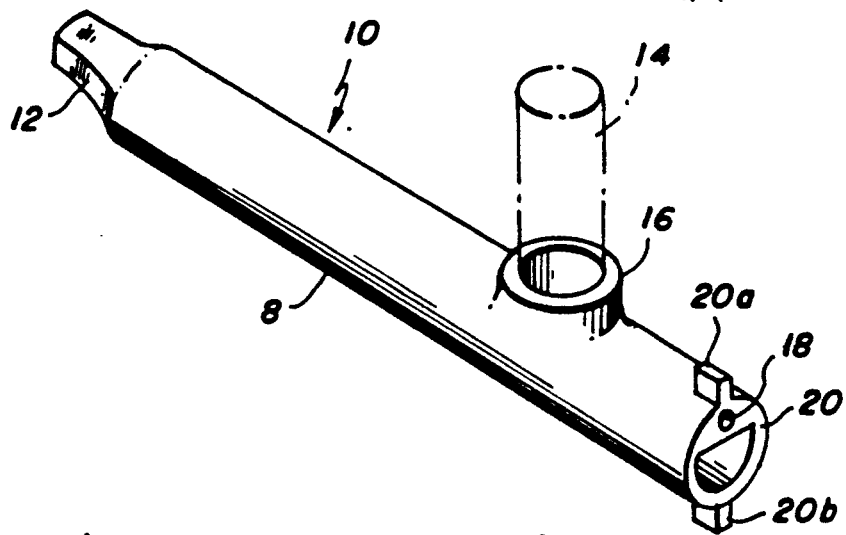
Figure 1B:
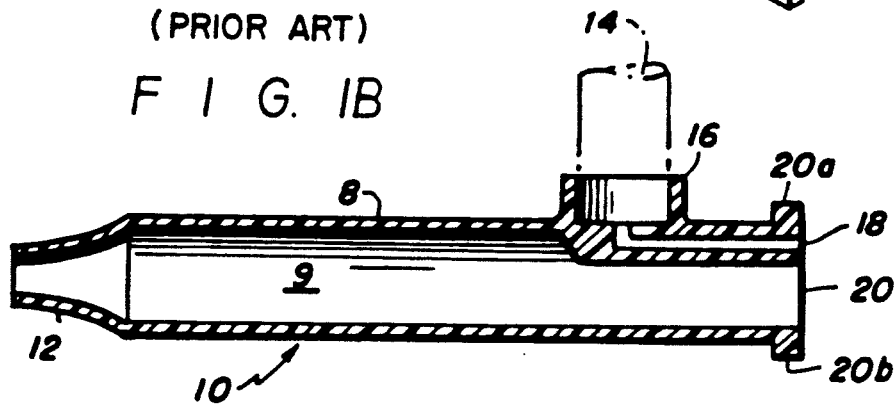
Figure 2:
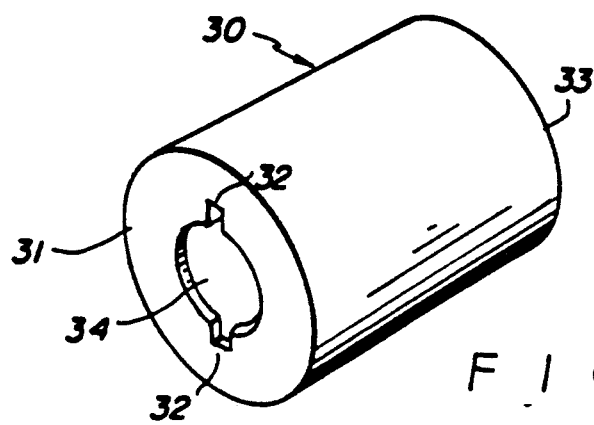

A mouthpiece is preferably coupled to the outlet aperture. Such mouthpiece is to space the users mouth from the chamber. One such mouthpiece is shown in FIGS. 1A and 1B. The proximal end 12 of the mouthpiece 10 is shaped to be accommodated in the mouth of the patient. In the preferred embodiment, a standard aerosol medication is administered from a metered dose inhaler 14 which is mounted to a coupling 16, which is designed to accommodate metered dose inhalers. Passage 18 directs the aerosol from the metered dose inhaler 14 out through the distal end of the mouthpiece. The distal end of the mouthpiece also has keys 20a and 20b, for example, which allow the mouthpiece 10 to be attached to the rigid chamber 30.

As shown in FIG. 2A, rigid chamber 30 which may be expandable and collapsible as described below, preferably has cut outs 32 which allow chamber 30 to be rigidly attached via keys 20A and 20B to the mouthpiece 10 (FIG. 3). Outlet aperture 34 allows the contents of metered dose inhaler 14 to be directed into chamber 30. End wall 33 of chamber 30 opposite end 31 has a plurality of small, rate limiting orifices 36a-i defined therethrough as can be seen in FIGS. 2B and 2C. In the preferred embodiment nine orifices, each about 0.020 inches in diameter are used. Depending on the age and health of the patient, orifices can be covered in any suitable manner, one at a time, until the volumetric flow rate for the patient is below 30 liters per minute. The covered orifices may be permanently sealed for a particular patient.

FIGS. 4A and 4B show an alternate embodiment of the invention. A rigid chamber 50, is provided having a proximal end 52, and a distal end 54, and a main body 58 therebetween. The proximal end 52 has an aperture 56, which is sized to accept standard disposable mouthpieces currently in use with hospital nebulizers. The body of the device 58 also has an opening 62 of a size suitable for coupling to an external source of aerosolized medication thereto. A means for closing the opening is further provided in accordance with the present invention. If the external source of aerosolized medication is retained in the opening, then that container will close the opening. In the alternative, the opening can be closed after delivery of medicament to the chamber. The means for closing is shown schematically by phantom box 57 and may be any conventional means for closing such as, for example, a piece of tape or a one-way valve structure. As yet a further alternative, the medicament can be delivered into the chamber through aperture 56. The distal end of the device 54, having a multiplicity of flow restricting orifices 60a-i (FIG. 4B).

Another alternate embodiment of the invention is shown in FIGS. 5A and 5B. The rigid chamber in this embodiment is collapsible, thereby making the invention more portable, and less noticeable when carried. Many patients, especially pediatric patients are embarrassed by their need to take medication, and this embodiment minimizes size and obtrusiveness. In FIG. 5A, the device is shown in its extended form, ready for use. The largest component piece, a truncated cone segment 70, has rate limiting orifices shown as 86a, 86i, and 86e. Other similar offices are provided but not shown in particular.

Truncated cone segments 70-78, nest inside one another and are thereby collapsible. Segment 78 also preferably has a circular flange 79, the diameter of which is at least the size of the small diameter of the largest piece 70. With this arrangement the pieces cannot inadvertently fall apart. A mouthpiece 80 is provided with a flared end sized to fit inside piece 78, and with an opening of sufficient diameter to allow a patient to inhale therethrough in an unrestricted manner. In the alternative the unit can be adapted to receive a mouthpiece or the mouthpiece of FIG. 1. The medicament can be delivered through mouthpiece 80, through an aperture in the chamber wall (not shown) or through the mouthpiece 10 if used therewith.

In the Examples which appear below, regular U-500 pork insulin (Eli Lilly) was aerosolized by a jet nebulizer (Raindrop: Puritan Bennett) connected to a compressed air source set at 30 psi. The timing of each aerosol actuation was controlled by a Rosenthal-French dosimeter and lasted for one second. In order to minimize oropharyngeal deposition of the insulin, aerosol was delivered into a holding chamber of the type described above which served as an extension device between the subject's mouth and the nebulizer. The distance between the subject's mouth and the nebulizer reduced aerosol velocity and, thus, impaction of particles in the mouth. Inspiratory flow rate at the time of aerosol inhalation was regulated to less than 30 and, preferably about 17 liters/minute by rate limiting orifices of the type described above. During inhalation, patients inspired from residual volume to total lung capacity.

Insulin units available to the mouth per inhalation from the delivery system were quantified prior to the beginning of the studies with human subjects. Insulin aerosol was generated during six consecutive actuations from 2 ml of U-500 pork insulin solution as described above into the holding chamber. After the sixth actuation, aerosol was inhaled from the holding chamber through a mouthpiece. Extraction of insulin from absolute filters attached to the mouthpiece indicated that 1.36±0.23 U was available for inhalation at the mouth following six actuations. To administer a dose of 0.2 U/kg body weight pork insulin to the mouth, subjects inhaled 6–13 times from the holding chamber, depending on their body weights. Each inhalation was proceeded by six actuations of the nebulizer.

As is illustrated by the Examples, a mean dose of approximately 0.2 U/kg BW of aerosolized insulin, delivered to the mouth for inhalation, effectively lowered blood glucose levels in the normal subjects and shifted blood glucose levels of five of the six NIDDM subjects to within the normal range (4.20–6.44 System International (SI) units). In the sixth subject (No. 8), the blood glucose level was lowered to 6.78 SI units, nearly within the normal range. A much smaller decrease in blood glucose levels was observed in three NIDDM subjects (Nos. 6–8) who inhaled saline aerosol (placebo) during another visit. These results indicate that the findings were not due to fasting per se. Variability in the magnitude of the glucose response between subjects was directly related to the dose of insulin deposited in the lungs, when the insulin dose was calculated on a per kilogram basis.

The results observed are in contrast to those reported by Wigley et al. and Elliott et al., who found that only one diabetic patient in the two studies combined achieved a normal blood glucose level after inhaling insulin. Those authors indicated that they delivered 240 U (0.5 ml of U 500/ml) and 50 U (50 breaths×2 ul/breath of U 500/ml) insulin, respectively, and concluded that variable and inefficient absorption of insulin across the lung mucosa could account for their poor results. These doses of insulin were estimated either from running the nebulizer dry of solution, or by determinations of weight loss in the nebulizer after each administration. Yet, it has been shown by Newman et al., "Deposition of Pressurized Aerosols in the Human Respiratory Tract", *Thorax*, 36: 52–55 (1981), using radioaerosol imaging techniques, that when pressurized aerosols are delivered directly into the mouth, only 10% of the inhaled fraction deposits beyond the oropharynx. The losses occur primarily because of impaction, resulting from high aerosol velocity and high inspiratory flow rate. In addition, in the study by Eliott et al., it is likely that most of the 50 U of insulin were lost in the holding chamber and testing of the delivery system. Because of these losses, the does delivered to the lungs in both studies was probably inadequate for normalization of blood glucose levels.

In contrast, in the present invention, a delivery system is utilized that adds distance between the patient's mouth and the aerosol generator, thereby decreasing aerosol velocity and impaction of particles at the mouth. More importantly, the present invention regulates inspiratory flow to a low flow rate of about 30 l/m or less and preferably as low as 17 l/m. The fraction of aerosol that deposits within the lungs is then quantified using, for example, gamma camera imaging technology. In particular, the present inventors calculated that a mean of 89.8±5% of the inhaled dose was actually deposited in the lungs. With a dose of 0.2 U/kg BW of insulin available at the mouth for inhalation, the deposited dose of insulin was similar to that given by subcutaneous administration, which probably accounts for the shift of blood glucose levels of the NIDDM subjects into the normal range.

The exact pharmacokinetics of insulin delivered through the lungs are not clear. The results of the Examples shown below illustrate that insulin absorption across the lung mucosa was more rapid than following subcutaneous administration, with serum insulin levels peaking at 35±31 minutes. With the exception of subjects 6 and 8, peak plasma insulin levels occurred within the first forty minutes after inhalation. Yet, blood levels did not return to baseline by the time the experiment was concluded in seven of the study subjects after a dose of approximately 0.2 U/kg BW of insulin. These findings may indicate both a fast and a slow component of insulin release across the lung mucosa. Variability in the kinetics of absorption of insulin across the lung mucosa was observed between individuals, but there did not appear to be any difference in absorption between the two normal subjects and the six NIDDM subjects. In addition, the drop in plasma glucose occurred in every subject and correlated closely to the insulin dose in a curvilinear relationship.

Aerosolized insulin administration was very well tolerated by the normal and NIDDM subjects, and there was a lack of any signs or symptoms, including adrenergic symptoms.

The present invention allows for the administration of a dose of 0.2 U/kg BW of aerosolized insulin that is deposited predominantly within the lungs and is well-tolerated. Administration of insulin in this manner, effectively lowered blood glucose levels in normal subjects and shifted blood glucose levels of NIDDM subjects to within the normal range. The glucose response to the dose of insulin administered as an aerosol was predictable when the dose was calculated on a per kilogram basis, and there did not appear to be significant variability between normal subjects and NIDDM subjects in absorption of insulin across the lung mucosa. These findings suggest a potentially new approach for controlling plasma sugar in human subjects.

The present invention can be illustrated by the use of the following non-limiting examples:

EXAMPLE I

Aerosol Delivery of Insulin to Subjects

The goal was to deliver between 0.1 and 0.2 U/kg BW pork insulin to the mouth for inhalation in these experiments. To accomplish this dosing regime, volunteers inhaled 5–13 times from the holding chamber. Each inhalation was preceded by six actuations of the nebulizer.

The precise protocol utilized for delivery of the insulin was as follows:

Two normal volunteers aged 39 and 44 years, respectively (subjects Nos. 1 and 2, Table 1), and six NIDDM volunteers aged 35–62 years (subjects Nos. 3–8, Table 1, shown below) participated in these studies. During a screening visit, subjects underwent routine spirometry testing and a diffusing capacity test (DLCO), in order to quantify their pulmonary functions. On the screening day, subjects also underwent a gamma camera imaging procedure in order to determine percent aerosol deposited within the lungs, using the holding chamber and nebulizer as described above. Subjects first inhaled one breath of a radioaerosol, generated from a 0.9% saline solution containing 8–12 millicuries of technetium 99-m sulfur colloid by the above delivery system, through an absolute filter. Activity detected on this filter was used to quantify the dose of radioactivity available per inspiration at the mouth. Then, subjects inhaled one to two breaths without the filter. After each inhalation, they exhaled into another absolute filter to collect the exhaled fraction. The total amount of radioaerosol delivered to the mouth did not exceed 60 microcuries (uCi), which resulted in a radiation absorbed lung dose <22.5 mrads.

Immediately following radioaerosol inhalation, patients were scanned with a large field of view GE STARCAM camera for ten minute imaging of the anterior chest and oropharynx. Images were acquired and processed in a 256×256 picture element matrix using a GE STARCAM computer. Activity (counts per minute) detected on the exhalation filter, within the oropharynx, and within the stomach (activity which could only have originated from aerosol deposited in the mouth) were expressed as a percent of the inhaled fraction and added together. The difference between this total and 100% was determined to be the percent of aerosol deposited below the larynx.

Insulin aerosol was later generated and delivered by the same type of nebulizer and holding chamber used to generate and deliver the radioaerosol. Inspiratory flow was also regulated at the same low rates. Because the delivery system and flow rates were the same, it was assumed that the fraction of insulin aerosol deposited within the lungs was the same as that of the radioaerosol.

None of the subjects had a history of asthma or other lung diseases and all were nonsmokers. No one was on or had ever been on insulin treatment. Subjects 3, 4 and 6 were medicated with Glyburide 10 mg/day, 15 mg/day, and 5 mg/day, respectively. Subject No. 5 was treated with Diabinese 750 mg/day. Subject No. 7 was medicated with Glyburide 20 mg/day and Subject No. 8 was unmedicated. Insulin administration was carried out in a fasting state. Patients were off oral Glyburide for 2 days and off Diabinese for 4 days, prior to inhaling insulin. During the study, blood samples were collected every 5 minutes for 60 minutes and every 10 minutes, thereafter, for up to 200 minutes from an indwelling venous line in order to measure blood glucose and insulin levels. Blood samples were assessed at the time of collection for glucose levels with a glucose meter (Accuchek). Determinations of plasma glucose levels were also obtained from photometric reaction with glucose hexokinase using an Hitachi 736 and 737 chemical analyzer (Boehringer Mannheim Diagnostics). The reference range for fasting adults using this technique and equipment is 3.92–6.44 SI units. Serum insulin levels were determined by antibody-coated tube RIA kits as described above. The expected range of values for normals in the fasting state, as provided by Diagnostics Products Corp., is 18–210 SI units. An IV saline solution was running, 50% glucose was available in case the blood glucose level decreased rapidly, and a diabetologist was present during the study. Normal subjects inhaled approximately a 0.1 U/kg BW dose and a 0.2 U/kg BW dose of insulin on two different occasions. NIDDM subjects inhaled approximately a 0.2 U/kg BW dose of insulin once. Three NIDDM subjects (Nos. 6–8 ) inhaled saline aerosol (placebo) delivered using the same protocol as insulin aerosol, in order to determine percent decrease in blood glucose during the fasting period. Studies were performed in the Johns Hopkins Outpatient Clinical Research Center. All patients who participated in these experiments gave informed consent to a written description of the study, which was approved by the Institutional Review Board.

When averaging decreases in blood glucose levels the data were normalized in terms of percent change from baseline. When averaging increases in blood insulin levels, the geometric mean (base $log_{10}$) was determined after the data were normalized by logarithmic transformation. Mean values for blood glucose levels, blood insulin levels, and average time to peak insulin levels or maximum decrease in glucose levels include data following the second dose of insulin for subjects No. 1 and 2 and the single dose for subjects Nos. 3–8. A Spearman-rank correlation test was used to determine the relationship between maximum percent decrease in glucose and the dose of inhaled insulin.

All subjects demonstrated normal pulmonary functions and DLCO measurements. Gamma camera scans of the respiratory tract indicated that deposition of the radioaerosol was maximized in the lungs of each of these subjects. The fraction of aerosol deposited below the larynx ranged from 82.4 to 96.0% of the inhaled dose. Mean (±s.d.) deposition was 89.8±5.0% of the inhaled fraction. A mean of 4.2±2.9% was exhaled.

The dose of insulin that was delivered to the mouth, for each of the normal subjects and NIDDM subjects as determined from the filter experiments described above, was calculated in terms of body weight and is shown in Table 2, below. Subjects inspired regular U-500 pork insulin in doses that ranged from 0.09 U/kg BW to 0.23 U/kg BW. Mean insulin dose was 0.21±0.01 U/kg BW.

TABLE 1

| Subject Number | Age (years) | Height (meters) | Weight (kg) | Sex | Medications |
|---|---|---|---|---|---|
| NORMAL SUBJECTS | | | | | |
| 1 | 39 | 1.90 | 86.62 | M | — |
| 2 | 44 | 1.66 | 64.40 | F | — |
| NIDDM SUBJECTS | | | | | |
| 3 | 42 | 1.80 | 78.68 | M | Glyburide 10 mg/day |
| 4 | 43 | 1.79 | 70.75 | M | Glyburide 15 mg/day |
| 5 | 62 | 1.55 | 57.14 | F | Glyburide 750 mg/day |
| 6 | 47 | 1.79 | 87.08 | M | Glyburide 5 mg/day |
| 7 | 35 | 1.68 | 54.40 | M | Glyburide 20 mg/day |
| 8 | 53 | 1.83 | 90.30 | M | — |
| x = | 46 | 1.75 | 73.7 | | |
| s.d = | 8 | 0.11 | 14.1 | | |

TABLE 2

| Subject Number | Baseline Insulin Level (SI units) | log | Insulin Dose Delivered by MDS (u/kgBW) | Peak Insulin Level (SI units) | log | Time to Peak Insulin Level (minutes) |
|---|---|---|---|---|---|---|
| NORMAL SUBJECTS | | | | | | |
| 1 (first dose) | 54* | 1.7324* | 0.09* | 138* | 2.1399* | 10* |
| 1 (second dose) | 66* | 1.8195 | 0.19 | 216 | 2.3345 | 35 |
| 2 (first dose) | 60* | 1.7782* | 0.11* | 300* | 2.4771* | 5 |
| 2 (second dose) | 87 | 1.9395 | 0.21 | 216 | 2.3345 | 5 |
| NIDDM SUBJECTS | | | | | | |
| 3 | 150 | 2.1761 | 0.21 | 588 | 2.7694 | 5 |
| 4 | 72 | 1.8573 | 0.23 | 198 | 2.2967 | 15 |
| 5 | 81 | 1.9085 | 0.21 | 204 | 2.3096 | 40 |

TABLE 2-continued

| Subject Number | Baseline Insulin Level (SI units) | log | Insulin Dose Delivered by MDS (u/kgBW) | Peak Insulin Level (SI units) | log | Time to Peak Insulin Level (minutes) |
|---|---|---|---|---|---|---|
| 6 | 75 | 1.8751 | 0.20 | 246 | 2.3909 | 52 |
| 7 | 48 | 1.6812 | 0.20 | 114 | 2.0569 | 25 |
| 8 | 42 | 1.6232 | 0.20 | 564 | 2.7513 | 100 |
| x = | geometric mean = 72 | 1.8601 | 0.21 | geometric mean = 254 | 2.4055 | 35 |
| s.d. = | | 0.1684 | 0.01 | | 0.2405 | 31 |

*Not included in mean calculations
MDS = Medication Delivery System

EXAMPLE II

Comparison of Blood Insulin Levels Prior and Subsequent to Insulin Inhalation After the protocol described in Example I was carried out, a comparison was made between the level of insulin found in the blood before and after aerosol administration of the insulin. (Table 2)

In particular, the average fasting blood insulin level for normal subject No. 1 was 54 and 66 SI units for study days 1 and 2, and for subject No. 2 was 60 and 87 SI units on the two study days, respectively. Baseline levels for the six NIDDM subjects were 150, 72, 81, 75, 48 and 42 SI units respectively. The geometric mean fasting insulin level for the eight subjects was 72 SI units.

Insulin levels for subject No. 1 peaked at 138 and 216 SI units after inhaling 0.09 and 0.19 U/kg BW of insulin, respectively. Insulin levels for subject No. 2 peaked at 300 and 216 SI units after inhaling 0.11 and 0.21 U/kg BW of insulin, respectively. Peak insulin levels for the NIDDM subjects were 588, 198, 204, 246, 114 and 564 SI units after inhaling 0.21, 0.23, 0.21, 0.20, 0.20 and 0.20 U/kg BW of insulin, respectively. Blood insulin levels peaked between five and one hundred minutes post inhalation. The average time to peak insulin level was $35 \pm 31$ minutes. After insulin inhalation, the geometric mean blood insulin level for the eight subjects rose to 254 SI units.

It should also be noted that insulin aerosol was well-tolerated. No adverse symptoms from the respiratory tract were reported or signs observed. Moreover, none of the subjects had adrenergic, hypoglycemic symptoms following insulin administration. Only one normal subject complained of being hungry.

EXAMPLE III

Comparison of Blood Glucose Levels Prior and Subsequent to Insulin Inhalation After the method described in Example I was performed, a comparison of blood glucose levels prior and subsequent to the aerosol administration of the insulin was undertaken.

The average fasting blood glucose levels for normal subject No. 1 was 4.70 SI units on both study days, and for subject No. 2 was 3.95 and 4.34 SI units on study days one and two, respectively. The baseline levels for the six NIDDM subjects were 10.58, 16.58, 12.12, 9.27, 13.94 and 13.30, respectively.

Glucose levels for normal subject No. 1 decreased to 4.09 and 3.08 SI units after inhaling 0.09 and 0.19 U/kg BW of aerosolized insulin, respectively. Glucose levels for normal subject No. 2 decreased to 3.14 and 2.24 SI units after inhaling 0.11 and 0.21 U/kg BW of insulin, respectively. Glucose levels for the NIDDM subjects decreased to 6.05, 4.82, 5.71, 4.26, 5.49, and 6.78 SI units after inhaling 0.21, 0.23, 0.21, 0.20, 0.20 and 0.20 U/kg BW of insulin, respectively. The time to 10% decrease in plasma glucose averaged $36 \pm 15$ minutes (Table 3, shown below). The maximum effect of inhaled insulin on glucose levels in both normal and NIDDM subjects occurred slowly over a variable time period ranging from 40 to 200 minutes. The average time to maximum decrease in blood glucose was $138 \pm 46$ minutes. Maximum decrease in glucose from baseline for all subjects is shown in Table 3, and ranged from 13 to 71%. Mean decrease was $52 \pm 10\%:41 \pm 10\%$ for the normals subjects and $55 \pm 10\%$ for the NIDDM subjects, following the administration of 0.2 U/kg BW of insulin.

Maximum percent decrease in glucose was significantly correlated with the dose of inhaled insulin, calculated on a per kilogram basis ($r_S = 0.68$; $p < 0.05$).

TABLE 3

| Subject Number | Maximum Decrease in Glucose (% of Baseline) | Time to 10% Decrease in Glucose (Minutes) | Time to Lowest Glucose Level (Minutes) |
|---|---|---|---|
| NORMAL SUBJECTS | | | |
| 1 (first dose) | 13* | 35* | 80* |
| 1 (second dose) | 34 | 50 | 140 |
| 2 (first dose) | 20* | 5* | 40* |
| 2 (second dose) | 48 | 15 | 40 |
| NIDDM SUBJECTS | | | |
| 3 | 43 | 30 | 150 |
| 4 | 71 | 30 | 160 |
| 5 | 53 | 40 | 200 |
| 6 | 54 | 42 | 140 |
| 7 | 61 | 20 | 120 |
| 8 | 49 | 60 | 150 |
| x = | 52 | 36 | 138 |

TABLE 3-continued

| Subject Number | Maximum Decrease in Glucose (% of Baseline) | Time to 10% Decrease in Glucose (Minutes) | Time to Lowest Glucose Level (Minutes) |
| --- | --- | --- | --- |
| sd = | 11 | 15 | 46 |

*Not included in mean calculations

EXAMPLE IV

Blood Glucose Levels Subsequent to Saline Inhalation

As a control, several subjects were administered saline (placebo) in aerosol form rather than insulin. Fasting blood glucose levels were 16.35, 17.70 and 12.01 SI units, respectively. Glucose levels decreased to 15.57, 13.89 and 10.70 SI units after saline inhalation. These decreases represented a 5, 22 and 11% change in blood glucose levels from baseline, respectively. Percent decrease in blood glucose was substantially greater following insulin inhalation, with 54, 61 and 49%, respectively.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A method for delivering insulin for absorption via the lungs of a patient, comprising the steps of:

determining a therapeutically effective amount of said insulin, consistent with the body weight and condition of the patient;

determining an effective number of inhalations required by a patient for inspiration of said therapeutically effective amount of insulin;

providing an inhaler device having a chamber for receiving aerosolized insulin to be inhaled and means for selectively restricting gas flow into said chamber;

providing aerosolized insulin at a regulated inspiratory flow rate of below 30 liters/minute;

delivering a mean dose of aerosolized insulin comprising said therapeutically effective amount of insulin to the patient for inspiration;

inhaling said mean does of aerosolized insulin from said inhaler device at said regulated inspiratory flow rate, said regulated inspiratory flow being selected to maximize the amount of aerosolized insulin deposited for absorption via the lungs into the bloodstream of the patient, whereby a therapeutically effective amount of said insulin, consistent with the body weight and condition of the patient, is inhaled and absorbed into the bloodstream of the patient.

2. The method of claim 1, wherein said flow rate is 17 liters/min.

3. The method of claim 1, wherein the patient's mouth is positioned in fluid communication with the chamber at a present distance from the chamber.

* * * * *